US010360674B2

(12) United States Patent
Contini et al.

(10) Patent No.: US 10,360,674 B2
(45) Date of Patent: Jul. 23, 2019

(54) FLOW ANALYSIS IN 4D MR IMAGE DATA

(71) Applicant: PIE MEDICAL IMAGING B.V., Maastricht (NL)

(72) Inventors: Enrico Contini, Maastricht (NL); Jean-Paul Aben, Limbricht (NL); Dennis Koehn, Voerendaal (NL); Rianne Reinartz, Neerbeek (NL)

(73) Assignee: PIE MEDICAL IMAGING B.V., Maastricht (NL)

( * ) Notice: Subject to any disclaimer, the term of this patent is extended or adjusted under 35 U.S.C. 154(b) by 731 days.

(21) Appl. No.: 15/091,964

(22) Filed: Apr. 6, 2016

(65) Prior Publication Data
US 2016/0314581 A1    Oct. 27, 2016

(30) Foreign Application Priority Data
Apr. 24, 2015  (EP) .................................... 15164979

(51) Int. Cl.
*G06T 7/00* (2017.01)
*A61B 5/055* (2006.01)
(Continued)

(52) U.S. Cl.
CPC ............ *G06T 7/0012* (2013.01); *A61B 5/026* (2013.01); *A61B 5/055* (2013.01); *G06T 7/248* (2017.01);
(Continued)

(58) Field of Classification Search
CPC ................... A61B 5/026; A61B 5/055; G06T 2207/10088; G06T 2207/10096;
(Continued)

(56) References Cited

U.S. PATENT DOCUMENTS 6,252,402 B1  6/2001 Sanfilippo et al.
7,332,912 B2  2/2008 Pittaluga et al.
(Continued)

OTHER PUBLICATIONS

"A Collaborative Resource to Build Consensus for Automated Left Ventricle Segmentation of Cardiac MR Images", Suinesiaputra et al, Medical Image Analysis, Jan. 2014, vol. 18, Issue 1, pp. 50-62.
(Continued)

*Primary Examiner* — Michael T Rozanski
(74) *Attorney, Agent, or Firm* — Gordon & Jacobson, P.C.

(57) ABSTRACT

A method is provided for flow analysis in a target volume of a moving organ, which involves a sequence of first volumetric image data sets that include structural information and three-directional velocity information of the target volume and a sequence of second volumetric image data sets that include structural information of the target volume. The method involves tracking a feature of interest within the sequence of the second volumetric data sets, determining time varying spatial orientation of a plane containing the feature of interest in the sequence of the first volumetric image data sets by transferring the plane from the second volumetric image data sets to the first volumetric image data sets, reformatting the three-directional velocity information into one-directional velocity information on the plane, and performing bi-dimensional quantitative flow analysis using the one-directional velocity information. A corresponding apparatus and computer program are also disclosed and claimed.

15 Claims, 8 Drawing Sheets

(51) Int. Cl.
*G06T 7/60* (2017.01)
*A61B 5/026* (2006.01)
*G06T 7/246* (2017.01)

(52) U.S. Cl.
CPC .............. *G06T 2207/10088* (2013.01); *G06T 2207/10096* (2013.01); *G06T 2207/30048* (2013.01); *G06T 2207/30104* (2013.01)

(58) Field of Classification Search
CPC . G06T 2207/30048; G06T 2207/30104; G06T 7/0012; G06T 7/248
See application file for complete search history.

(56) References Cited

U.S. PATENT DOCUMENTS

| | | |
|---|---|---|
| 2010/0014739 A1 | 1/2010 | Kiraly |
| 2011/0103665 A1 | 5/2011 | Gulsun et al. |

OTHER PUBLICATIONS

"A Simplified B-Spline Computation Routine," Lee, Computing 1982, vol. 29, Issue 4, pp. 365-371.
"Accurate and Reproducible Mitral Valvular Bood Flow Measurement with Three-Directional Velocity-Encoded Magnetic Resonance Imaging", Westenberg et al. Journal of Cardiovascular Magnetic Resonance, 2004; vol. 6, No. 4, pp. 767-776.
"Automated Detection of Left Ventricle in 4D MR Images: Experience From a Large Study," Lin et al., Medical Image Computing and Computer-Assisted Intervention—MICCAI 2006, vol. 4190 of the series Lecture Notes in Computer Science, Springer, pp. 728-735.
"Characterization and Improved Quantification of Left Ventricular Inflow Using Streamline Visualization With 4DFlow MRI in Healthy Controls and Patients After Atrioventricular Septal Defect Correction", Calkoen et al., Journal of Magnetic Resonance Imaging, 2014, 41(6), pp. 1512-1520.
"Deformable Motion Tracking of Cardiac Structures (DEMOTRACS) for Improved MR Imaging", Dewan et al., IEEE Conference on Computer Vision and Pattern Recognition, 2007.
"Flow Analysis in Cardiac Chambers Combining Phase Contrast, 3D Tagged and Cine MRI", Radomir Chabiniok et al, Jun. 20, 2013, Functional Imaging and Modeling of the Heart, Springer Berlin Heidelberg, Berlin, Heidelberg, pp. 360-369.
"Flow Assessment Through Four Heart Valves Simultaneously Using 3-Dimensional 3-Directional Velocity-Encoded Magnetic Resonance Imaging with Retrospective Valve Tracking in Healthy Volunteers and Patients with Valvular Regurgitation", Roes et al, Investigative Radiology 2009; 44: 669-674.
"Layered Spatio-Temporal Forests for Left Ventricle Segmentation from 4D Cardiac MRI Data," Margeta et al, Statistical Atlases and Computational Models of the Heart. Imaging and Modelling Challenges, vol. 7085 of the series Lecture Notes in Computer Science, Springer, pp. 109-119.
"Mitral Valve and Tricuspid Valve Blood Flow: Accurate Quantification with 3D Velocity-Encoded MR Imaging with Retrospective Valve Tracking", Westenberg et al Radiology 2008; 249:792-800.
MR Velocity Mapping of Tricuspid Flow: Correction for Through-Plane Motion. Kayser, H. W. M., Stoel, B. C., Van Der Wall, E. E., Van Geest, R. J. D. and De Roos, A. (1997), J. Magn. Reson. Imaging, 7: 669-673.
"New Respiratory Gating Technique for Whole Heart Cine Imaging: Integration of a Navigator Slice in Steady State Free Precession Sequences," Uribe et al., J Magn Reson Imaging., Jul. 2011, 34(1), pp. 211-219.
"Time-Resolved Three-Dimensional Phase-Contrast MRI," Markl et al., Journal of Magnetic Resonance Imaging, Sep. 2003, 18(3), p. 396 and J Magn Reson Imaging., Apr. 2003, 17(4), p. 499-506.
"Three-Dimensional Dynamic Assessment of Tricuspid and Mitral Annuli Using Cardiovascular Magnetic Resonance", Maffessanti et al., European Heart Journal—Cardiovascular Imaging (2013), vol. 14, Issue 10, pp. 986-995.
"Volumetric Image Registration by Template Matching," Ding et al, Proc. SPIE 3979, Medical Imaging 2000: Image Processing, 1235 (Jun. 6, 2000).
"Whole Left Ventricular Functional Assessment from Two Minutes Free Breathing Multi-Slice CINE Acquisition", Usman et al., Physics in Medicine & Biology, Apr. 2015, 60(7), pp. N93-N107.

FLOW ANALYSIS IN 4D MR IMAGE DATA

CROSS-REFERENCE TO RELATED APPLICATIONS

The present application claims priority from EP Patent Appl. No. 15164979.5, filed on Apr. 24, 2015, herein incorporated by reference in its entirety.

BACKGROUND

1. Field

The embodiments herein relate to the technical field of medical imaging, particularly MR cardio imaging, although it can find application in any field where there is the need to quantify flow in a moving object such as in non destructive testing applications.

2. State of the Art

The accurate study and characterization of blood flow patterns and pathophysiology in the cardiac valves and in the main vessels of the human anatomy play a role of primary importance in the diagnosis and treatment of cardiovascular dysfunctions.

Stenosis, inlet and outlet valve regurgitation or congenital defects represent few examples in which the cardiovascular function needs a close imaging follow-up to assess the severity of the symptoms and the consequent optimal timing and type of surgical intervention.

One of the most used techniques to analyze blood flow in clinical setting is flow sensitive Magnetic Resonance (MR) imaging.

The intrinsic sensitivity of MR to flow allows reliable quantification of vascular hemodynamics and qualitative delineation of flow patterns, without the restriction to anatomic coverage or flow directions. This is normally performed by the acquisition of a number of 2D phase-contrast Magnetic Resonance Imaging (MRI) planes, also known as 2D MR Flow.

However, this method requires careful planning of the 2D phase-contrast MR image acquisition planes by an MR operator. For example, for each valve that is being assessed, the operator needs to carefully position a plane that is used for acquisition. The planning of this plane is of great importance because this plane is static and needs to be placed perpendicular to the blood flow. The fact that the acquisition plane is static means the plane does not move during the entire acquisition of the data. Even if the operator manages to place the plane optimally within the dataset, certain problems still arise. For instance, out of plane motion will occur. This out of plane motion (through plane motion i.e., motion in the longitudinal direction through the acquisition plane positioned at the heart valve of interest) is a result of movement of the heart during the cardiac cycle. This is a major obstacle for accurate flow estimations, especially in transvalvular regions as reported by previous studies such as Kayser et al., "*MR velocity mapping of tricuspid flow: correction for through-plane motion*," J Magn Reson Imaging 1997; 7: 669-673. This through plane motion results in unusable data hence data is acquired in the static plane but this plane does not contain the correct features (i.e. the valve) anymore. Therefore, this also results in the inability to make a diagnosis based on this data.

Furthermore, due to this high operator dependency, incorrect planning occurs regularly—even in high patient volume centers—, making clinical assessment difficult, and potentially hampering a correct diagnosis.

Furthermore, the operator needs previous knowledge of the flow-encoding direction in order to position the acquisition plane perpendicular to the blood flow. All these aspects result in a time-consuming and error prone process.

Time resolved three dimensional phase contrast MRI (4D MR flow) is an evolving imaging technique used for evaluation of multidirectional flow velocity data. In 4D MR flow, anatomical and three-directional velocity information are acquired for each voxel within a 3D isotropic volume over time.

This type of data allows the analysis of the blood flow from any spatial oriented plane. Therefore, the aforementioned problems of a static analysis plane does not hold anymore, since the plane can be repositioned at each acquired time point (i.e. at each acquired phase during the cardiac cycle) to tightly follow the cardiac and respiratory movements. Due to the cardiac and respiratory movement compensation and by centering the analysis plane for the object of interest, through plane motion will therefore not occur anymore as taught by Westenberg et al., "*Accurate and Reproducible mitral valvular blood flow measurement with three-directional velocity-encoded magnetic resonance imaging*," J Cardiovasc Magn Reson., 2004; 6:767-776.

Repositioning of the analysis plane during the cardiac cycle requires tracking of anatomical landmarks. A downside of the 4D MR Flow imaging technique is the limited signal to noise ratio of the anatomical data. This results in poor detailed outlining of anatomical structures. Therefore, a different strategy has to be adopted to efficiently track anatomical structures movements.

Several authors addressed the problem by manually identifying the valve position on each time frame on two additional MR sequences, for instance Westenberg et al., "*Mitral valve and tricuspid valve blood flow: accurate quantification with 3D velocity-encoded MR imaging with retrospective valve tracking*," Radiology 2008; 249:792-800 and Roes et al., "*Flow assessment through four heart valves simultaneously using 3-dimensional 3-directional velocity-encoded magnetic resonance imaging with retrospective valve tracking in healthy volunteers and patients with valvular regurgitation*," Invest Radiol 2009; 44: 669-674. Their method requires two additional long axis cine MR acquisitions acquired orthogonal to each other and intersecting with the valve of interest, e.g. for the mitral valve (as shown in FIG. 2) a left ventricular two-chamber and four-chamber cine MRI acquisition are required. That is for each valve, two long axis cine datasets have to be acquired. Accurate planning of these long axis cine images is needed to avoid out of plane motion of the valve of interest.

Furthermore, this approach of manual annotation of valve locations during the cardiac cycle has two important limitations. Manual annotation makes the tracking results user dependent and scarcely reproducible, and also results in large intra- and inter observer variations.

The second limitation of manual annotation of valve location is the long process time required for each case. Considering these limitations, manual valve tracking is impracticable for clinical routine.

In another work Dewan et al., "*Deformable Motion Tracking of Cardiac Structures (DEMOTRACS) for Improved MR Imaging*", IEEE Conference on Computer Vision and Pattern Recognition, 2007, the cardiac motion information was estimated by valve tracking in MR images acquired during an initial scan (Long Axis views), which can then be used to adaptively re-position the acquisition slice during 2D MR Flow acquisition.

The tracking method is based on a predefined database of manual identified anatomical landmarks. This method requires a database with identified anatomical landmarks for specific scan orientations (long axis views). This makes this method heavily dependent on the content of the predefined database, acquisition method and long axis plane orientation.

Further, this work focuses on valve tracking for dynamic acquisition plane positioning for 2D MR Flow acquisitions only. This method is applied during a cardiac MR flow acquisition, with the patient inside the scanner. Errors in the valve tracking result in incorrect flow acquisitions and no diagnosis will be possible afterwards.

SUMMARY

It is thus an object of the embodiments herein to provide an improved method for accurate study and characterization of blood flow patterns in cardiac valves with minimal operator interaction.

In accordance with embodiments herein, systems, computer program products and computer implemented methods are provided for performing flow analysis in a target volume of a moving organ, such as the heart, from sequences of a first and a second magnetic resonance volumetric image data sets of such organ, which data sets are timely separated by a certain time interval, wherein the first volumetric image data set comprises structural information and three-directional velocity information of the target volume and the second volumetric image data sets comprises structural information of the target volume, the systems, program products and methods comprising, under control of one or more computer systems configured with specific executable instructions, a) determining at least one feature of interest in at least one volume data set of the sequence of second volumetric image data sets, for example, by receiving an input from a user or by performing automatic detection steps on at least one volume of the sequence of second volumetric image data sets (for example by segmenting the target and/or making a contour analysis of the same);

b) tracking the feature of interest within one or more volume data sets of the sequence of the second volumetric data sets, for example by matching multiple variable-size volumetric templates in the second volume data sets;

c) determining the spatial orientation over time of a plane containing the feature of interest in the sequence of the second volumetric data sets;

d) determining the spatial orientation over time of the plane containing the feature of interest in the sequence of the first volumetric data sets, for example by transferring the plane from the second volumetric data sets to the first volumetric data sets;

e) reformatting the three-directional velocity information into one-directional velocity information on the plane as determined in step d);

f) performing bi-dimensional quantitative flow analysis using the one-directional velocity information.

Embodiments employ the property of a new type of MR sequence, the so-called axial cine MR, whose image data consists of 3D volume with approximately isotropic voxels acquired at multiple time-point within the cardiac cycle. Acquisition of axial cine MR image data only requires the definition of a volume of interest and avoids careful planning of two dimensional (long axis) acquisition planes. Until now the axial cine MR image data is not commonly applied in cardiac MR imaging due to long scan time, respiratory motion artifacts and no optimal scan sequence is commonly available. Recently, breathing navigator sequences are developed to obtain the whole axial cine MR image data set during free breathing, Uribe et al., "*New Respiratory Gating Technique for Whole Heart Cine Imaging: Integration of a Navigator Slice in Steady State Free Precession Sequences*," J Magn Reson Imaging., July 2011, 34(1), pgs. 211-219. With respiratory navigator the acquisition time of an axial cine MR data set will be decreased and the image quality is improved, Usman et al., "*Whole left ventricular functional assessment from two minutes free breathing multi-slice CINE acquisition*," Phys Med Biol., April 2015, 60(7), pgs. N93-107. These recent developments will speed up the introduction of the axial cine MR image data into general cardiac MR examination. With that the axial cine MR image data can be used for e.g. functional analysis.

To solve the incorrect flow estimations based on 2D MR Flow acquisitions, or the user dependent and time consuming valve tracking workflow by use of long axis cine images for the benefit of quantitative flow analysis of 4D MR Flow data, an innovative work flow is proposed. This workflow simplifies the MR acquisition, improves accuracy and reproducibility and decreases analysis time.

In the workflow in accordance to embodiments herein, the benefits of 4D MR Flow data are combined with a single volumetric axial cine acquisition for tracking the valve location during the cardiac cycle. Replacement of multiple long axis acquisition with a single volumetric axial image set for tracking the valve location has several advantages.

First of all, the acquisition of an entire volume over time instead of a several series of long-axis images requires considerably less operator interaction, and therefore reduces the possibility of user error. The use of volumetric data gives the opportunity to track multiple valves without the need of 2D long-axis acquisitions for each valve of interest. Also because the information of all valves can be contained within one volumetric dataset, all information is gathered within the same cardiac state.

Secondly, using 3D volumetric data instead of simple 2D long-axis data for tracking the valve features represents a significant advantage. To track the position of the valve in the 3D space, at least two 2D long-axis cine MR images orthogonal to each other are required. Multiple long-axis images result from separate acquisitions in different breath-holds, therefore possible errors due to patient movement between the several 2D long-axis acquisitions can be present.

Using axial cine MR image data, the above mentioned possible source of errors are overcome, since this type of data is obtained from a single continuous acquisition.

Furthermore, the valve tracking can be performed during post processing within the axial cine MR images data instead of during the scanning time with a (static) acquisition plane. Because of this a potential error in the process can be easily identified and corrected, whereas if the valve tracking is performed during the scanning time, the data is unusable and no diagnosis can be performed until new data is acquired.

Embodiments also relate to a MR apparatus for acquiring volumetric images comprising an acquisition system for obtaining a cine of consecutive image volumes of the heart of a patient. The apparatus advantageously comprises a processing module programmed for performing the method according to embodiments herein to make a quantitative blood flow analysis. Particularly the apparatus is configured to acquire 4D flow images and axial cine images of a volume containing a heart valve with the processing module being programmed to determine the orientation of a valve plane, for example by performing valve tracking after the volume sequences have been acquired, in the axial cine images, locate such plane in the 4D flow images and make a bi-dimensional flow analysis based on velocity information as projected on such a valve plane.

Further improvements of the invention will form the subject of the dependent claims.

BRIEF DESCRIPTION OF THE DRAWINGS

The characteristics of the invention and the advantages derived therefrom will be more apparent from the following description of non-limiting embodiments, illustrated in the annexed drawings.

DETAILED DESCRIPTION OF ILLUSTRATIVE EMBODIMENT(S)

A magnetic resonance imaging (MRI) apparatus comprises an imaging unit configured to carry out sequential imaging. The apparatus applies a radio-frequency magnetic field onto a subject (i.e. patient) placed in a static magnetic field. A magnetic resonance signal generated from the subject is detected due to the application of the radio-frequency magnetic field. Using the detected signals an image is created.

The magnetic resonance imaging apparatus also includes a gradient coil that adds spatial positional information to a magnetic resonance signal by applying a gradient magnetic field onto the subject.

Using different combinations of radiofrequency pulses and gradients, different MRI sequences can be made. An MRI pulse sequence is a programmed set of changing magnetic gradients. Different pulse sequences allow the radiologist to image the same tissue in various ways, and combinations of sequences reveal important diagnostic information.

Figure 6:
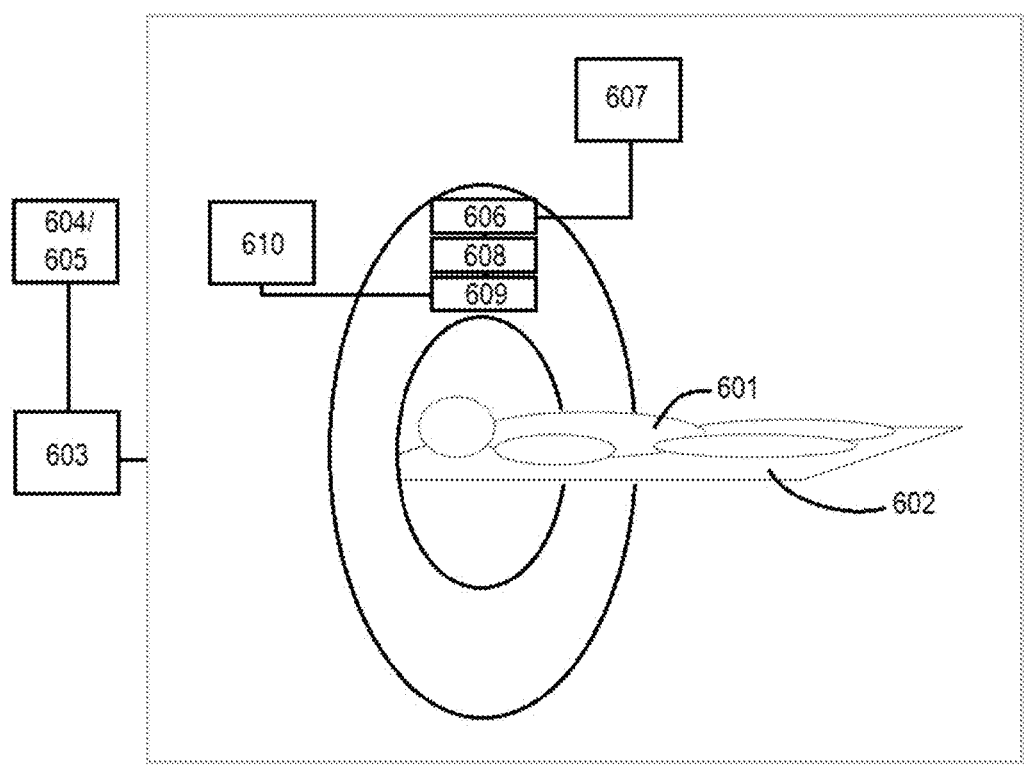
FIG. 6 illustrates an example of a high-level block diagram of an MR system.

FIG. 6 illustrates an example of a high-level block diagram of an MRI system.

Portions of the system (as defined by various functional blocks) may be implemented with dedicated hardware, analog and/or digital circuitry, and/or one or more processors operating program instructions stored in memory.

The MRI system of FIG. 6 includes an adjustable table 602 for a patient 601, a data processing module 603 and a magnet system 606.

The data processing module 603 includes one or more processors and memory that stores program instructions to direct the one or more processors to perform the operations described herein. The data processing module 603 also includes a display to present information to a user, such as the images, indicia, data and other information described herein and illustrated in the figures. The data processing module 603 also includes a user interface to receive inputs from the user in connection with operations herein, such as controlling operation of the imaging apparatus. For instance, scan parameters can be selected or altered, patient images may be displayed and post-processing can be performed, including, for example, region of interest measurements, flow quantification and visual and/or quantitative control selecting projection perspectives to be used when obtaining complementary images and the like. The data processing module 603 may correspond to or include portions of one or more of the systems described within the patents and publications referenced herein and incorporated by reference.

One of the key aspects of an MRI system is the magnet system 606. The magnet system 606 generally comprises a large tube or a cylindrical magnet. The magnet is typically an electromagnet made from coils of superconducting wire typically helium cooled. The flow of electrical current through these coils produces a magnetic field. Permanent magnets can be used as well. The magnetic field has a certain field strength measured in Tesla. An important aspect of the magnet system 606 is the homogeneity of the magnetic field. That is a magnetic field that changes very little over the specified region or volume.

However, due to manufacturing imperfections or intervention room problems such as nearby steel posts, distortions of the magnetic field may arise. These inhomogeneities are corrected using a shim system 607. The corrections can either be performed manually or automatically. U.S. Pat. Nos. 6,252,402 and 7,332,912 disclose examples of shimming techniques for systems based on permanent magnets.

In clinical MRI hydrogen atoms of the human body are of importance. The nucleus of each hydrogen atom possesses spin also called nuclear spin angular momentum. That is, the nucleus of the hydrogen atom constantly rotates around an axis at a constant rate. When placed inside a magnetic field the nucleus the rotation axis tilts to align with the magnetic field.

The strong static magnetic field produced by the magnet system 606 aligns the spins of each hydrogen atom of the human body in a certain frequency that is dependent on the strength of the magnetic field.

Next, a radio frequency system 609 emits a radio frequency pulse (RF-pulse) towards the part of the body being examined, tuned to a specific range of frequencies at which hydrogen protons move. This results in some of the hydrogen protons being moved 180 degrees out of alignment with the static magnetic field and being forced into phase with other hydrogen protons.

The radio frequency system 609 generally comprises transmitting coils. The transmitting coil is usually bunt into the body of the scanner and transmits the RF-signal, generating an effective field perpendicular to the main magnetic field.

The energy which is absorbed by different hydrogen atoms in the body is then echoed or reflected back out of the body. The gradient system 608 is switched on and off to measure the echoes reflecting black out of the patient 601 and thus to localize the tissue signals.

Generally, a gradient system 608 consists of one or multiple gradient coils and gradient amplifiers.

Gradient coils are usually loops of wire or thin conductive sheets on a cylindrical shell lying just inside the bore of an MRI scanner. When current is passed through these coils a secondary magnetic field is created. This gradient field slightly distorts the main magnetic field in a predictable pattern, causing the resonance frequency of protons to vary as a function of position.

Typically, three sets of gradients are used: the x-, y- and z- gradients. Each coil set is driven by an independent power amplifier and creates a gradient field whose z-component varies linearly along the x-, y- and z-direction respectively producing the orthogonal field distortion required for imaging.

A data acquisition system 610 then receives the echoes. The data acquisition system 610 is responsible for measuring the signals from the protons and digitizing them for later post-processing. In general, the data acquisition system 610 consists of a coil, a pre-amplifier and a signal processing system.

The coil detects the induced voltage form the protons following an RF-pulse. The coil is tuned to the particular frequency of the returning signal.

The pre-amplifier is a low-noise high gain amplifier located inside the magnet room or the coil itself in order to be able to process the signals produced by the protons.

Furthermore, the signal processing system provides for instance further amplification of the signal, demodulation into kHz signal, low-pass filer, divided into real and imaginary parts then detected by the analog-to-digital converters (ADC). By applying an Inverse Fourier transformation (IFT) that converts the signal from the protons as mathematical data (k-space) into a picture that can be interpreted by the clinician.

The storage 604 is used to store the patient images that have been acquired immediately after they have been reconstructed. This is typically done in a universal language (vendor independent) such as DICOM. The storage can be a hard disk or a PACS (picture archiving and communications system) server 605.

Velocity encoding gradient echo imaging, also known as phase contrast imaging, is an MRI technique for quantifying blood flow, hereinafter also referenced as 4D MR Flow acquisition. By measuring the phase shift that occurs as protons in the blood move through a magnetic field, the velocity and direction of the blood can be obtained. Details on the time resolved three dimensional phase contrast MRI sequence is published by M. Markl et al., "Time-Resolved Three-Dimensional Phase-Contrast MRI," J Magn Reson Imaging., September 2003, 18(3), pg. 396 and J Magn Reson Imaging., April 2003, 17(4), pg. 499-506, herein incorporated by reference in its entirety. Details on the axial cine MR sequence is published by Uribe et al., "*New Respiratory Gating Technique for Whole Heart Cine Imaging: Integration of a Navigator Slice in Steady State Free Precession Sequences,*" J Magn Reson Imaging., July 2011, 34(1), pgs. 211-219, herein incorporated by reference in its entirety.

Figure 7:
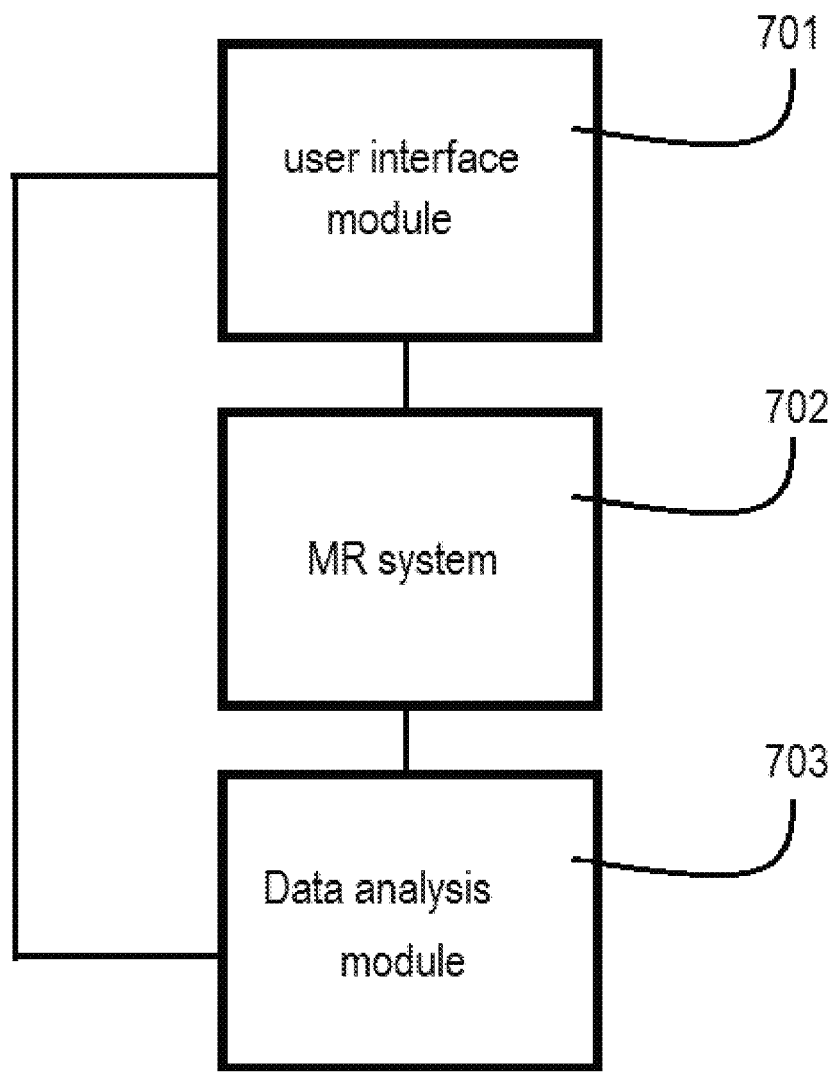
FIG. 7 is a functional block diagram of a system according to an embodiment herewith.

FIG. 7 is a functional block diagram of an exemplary 4D MR Flow acquisition in accordance to an embodiment herein which includes an MR system 702 that operates under commands from the user interface module and provide data to the data analysis module 703.

A clinician or other user acquires an MRI image of a patient 601 and stores this image on a hard disk 604 or a PACS server 605 in DICOM format.

The MRI system 702 acquires 4D MR Flow data of a volume of interest for instance the heart covering the four valves and cine MRI. The MR system typically includes a magnet system, a radio frequency system, a gradient system, a data acquisition system and a data storage.

The data analysis module 703 may be realized by a personal computer, workstation or other computer processing system. The data analysis module 703 processes the acquired 4D MR Flow data and the cine MR data of the MRI system 702 to generate, for instance, flow analysis quantification.

The user interface module 701 interacts with the user and communicates with the data analysis module 703. The user interface module 701 can include different kinds of input and output devices, such as a display screen for visual output, a touch screen for touch input, a mouse pointer or other pointing device for input, a microphone for speech input, a speaker for audio output, a keyboard and/or keypad for input, etc.

The data stored by the MRI system 702 may be used for accurate flow analysis performed by the data analysis module 703 in accordance with embodiments herein.

Figure 1A:
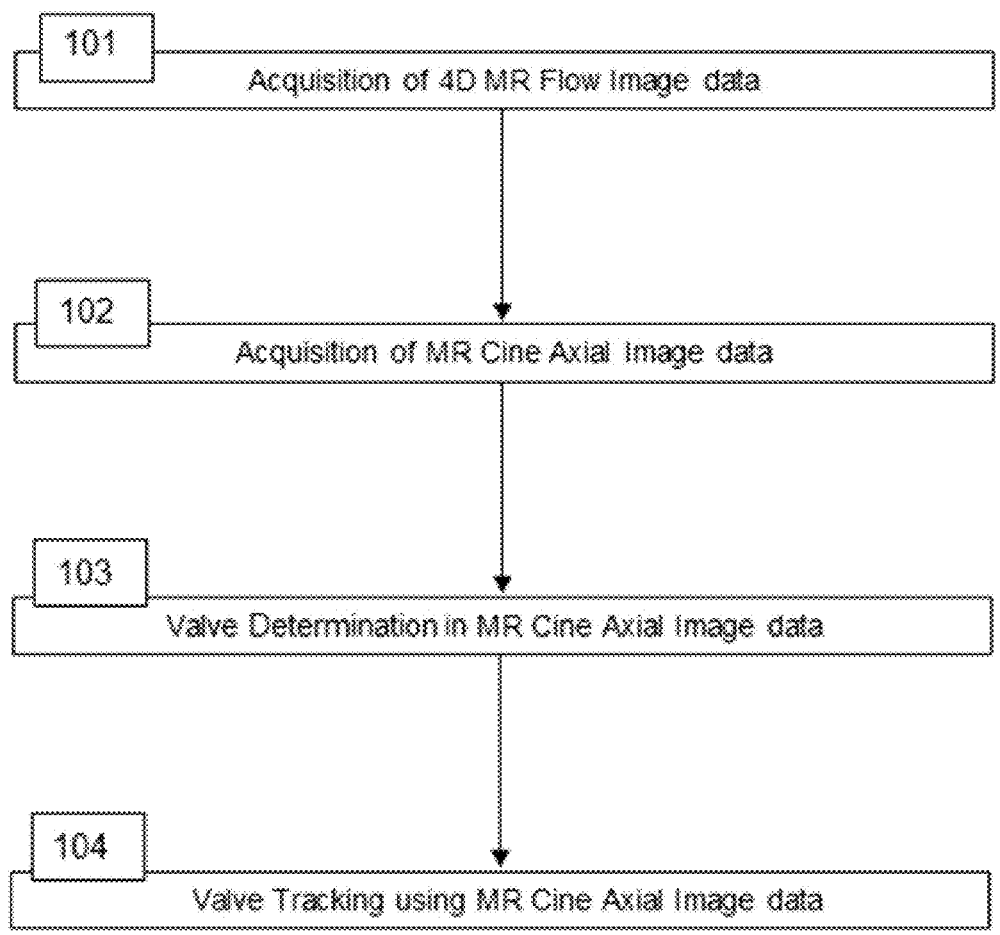
FIGS. 1a and 1b, collectively, shows a flowchart of the steps of an illustrative embodiment of the present disclosure.
Figure 1B:
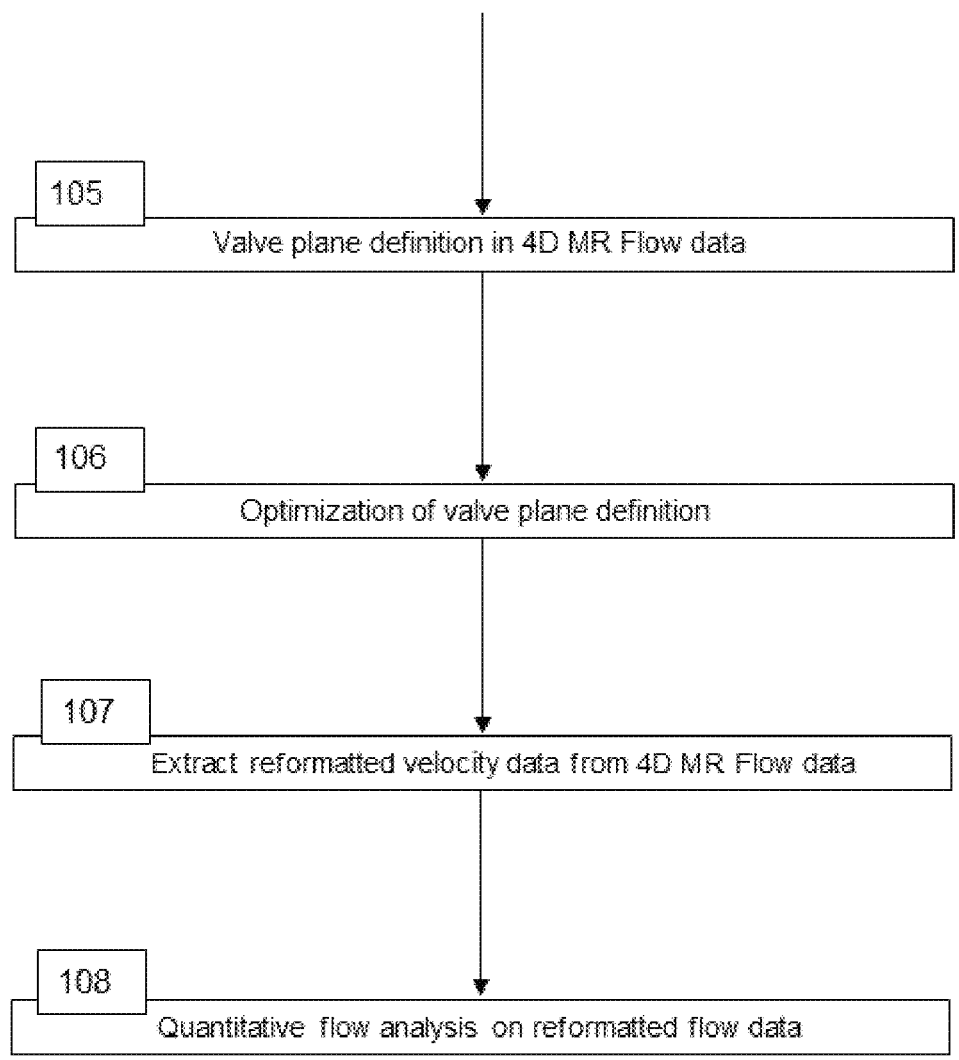
Figure 2:
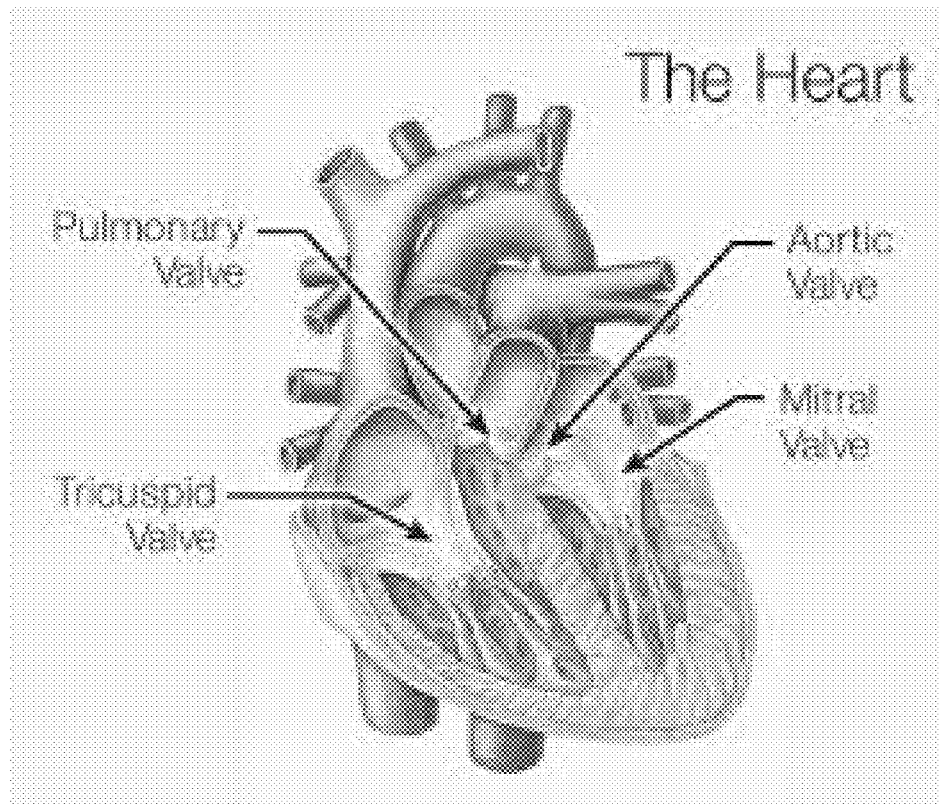
FIG. 2 shows the anatomy of the human heart, including the four valves.

FIGS. 1a and 1b shows a flow chart illustrating the operations according to an embodiment of the present application. The operations, typically performed by the data analysis module 703, can also be carried out by software code that is embodied in a computer product (for example, an optical disc or other form of persistent memory such as a USB drive or a network server). The software code can be directly loadable into the memory of a data processing system for carrying out the operations of FIGS. 1a and 1b.

During the scanning time, two sets of 4D MR image data are acquired by the processor or processors.

The first set consists of anatomical data and three-directional velocity information acquired for each pixel within a 3D isotropic volume over time, namely 4D MR flow (operation 101 of FIG. 1a). In this type of data, the blood flow through a plane can be studied on any arbitrary positioned plane within the acquired volume.

However, the scarce signal to noise ratio of the anatomical data represents a considerable obstacle in the identification of valve features. Therefore, a second set of whole heart cine MR images is acquired.

This set of 4D (3D+time) anatomical data consists of stacked high resolution axial cine-scan (step 102 of FIG. 1a). This stack replaces the more traditional long-axis cine MR acquisitions, therefore minimizing operator interaction and overcoming a possible spatial offset as described earlier.

Figure 3:
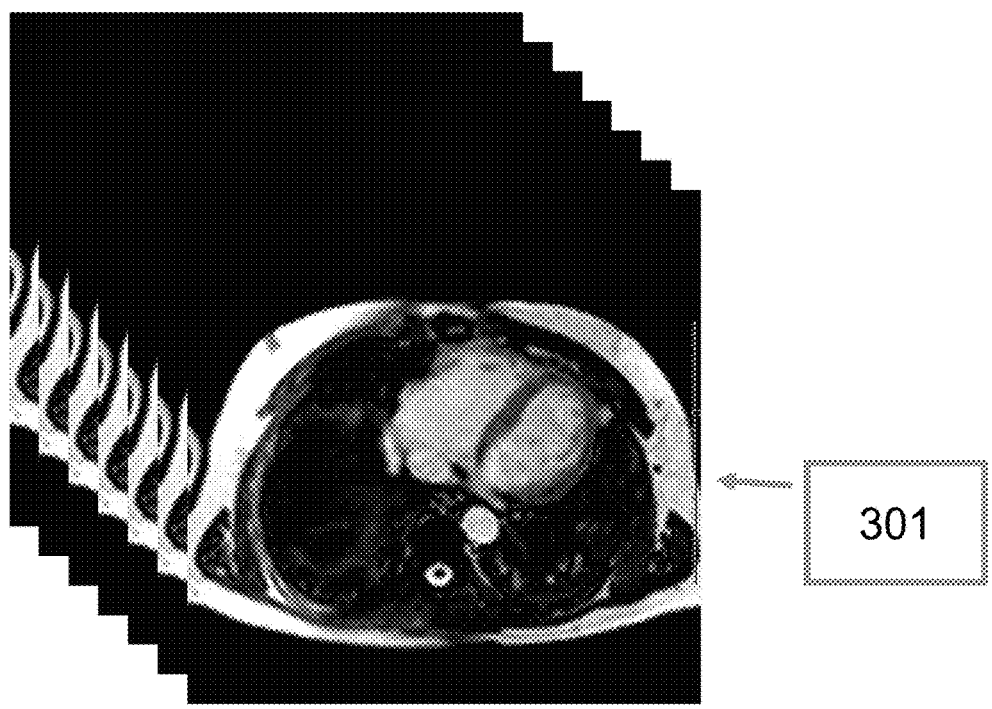
FIG. 3 shows a single axial cine MR image from the complete volumetric axial image set. The valvular position is manual annotated within a double oblique image (representing the long-axis) from the axial volumetric image set.
Figure 3:
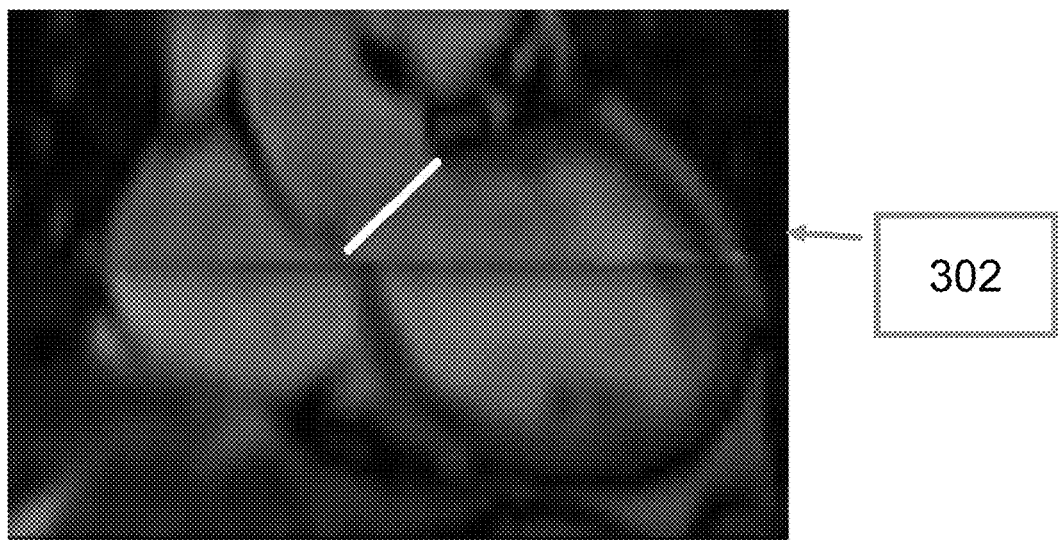

Before starting the valve tracking process, one or multiple valves of interest need to be determined within the axial cine MR image volume (operation 103 of FIG. 1a). The task can be completed by two approaches. The first approach is by valve landmarks determination through user interaction as shown in FIG. 3. Based on the volumetric axial cine MRI (301) a double oblique image is generated from the volumetric axial cine MRI representing a long-axis cut within the volumetric axial cine MRI. Within this double oblique image sequence (multiple time stamps) the user manually identifies the valve landmarks (valve plane) (302). The second approach makes use of automatic valve features detection.

A viable way to automatically identify the approximate position of the aortic and mitrel valve is to first localize and segment the left ventricle. There are several methods known in the art to perform left ventricle segmentation as described by Suinesiaputra et al "*A collaborative resource to build consensus for automated left ventricle segmentation of cardiac MR images,*" Medical Image Analysis, January 2014, Volume 18, Issue 1, pgs. 50-62, herein incorporated by reference in its entirety. These methods can easily be adapted for valve determination.

Another feasible method to achieve the automatic left ventricle segmentation is the one proposed by Margeta et al, "*Layered spatio-temporal forests for left ventricle segmentation from 4D cardiac MRI data,*" Statistical Atlases and Computational Models of the Heart. Imaging and Modelling Challenges, Volume 7085 of the series Lecture Notes in Computer Science, Springer, pgs. 109-119, herein incorporated by reference in its entirety. This method is based on a machine learning approach, using a double layer of random decision forests to classify the voxels of the 4D cardiac MR dataset. The images were treated directly as 3D+t volumes and the segmentation problem was defined as voxel-wise classification into myocardium and background.

The two classification layers were trained to segment the LV myocardium, each for a different purpose. The probability map from the first layer was mainly used to correct the cardiac sequences for acquisition pose differences and to estimate myocardial intensity for MRI intensity standardization. The second layer was then retrained on intensity and pose standardized images, and finally used for a more accurate final segmentation.

An alternative way to determine the approximate position of the mitrel and aortic valve into the axial cine MR data is the method proposed by Lin et al., "*Automated detection of Left Ventricle in 4D MR images: Experience form a Large Study,*" Medical Image Computing and Computer-Assisted Intervention—MICCAI 2006, Volume 4190 of the series Lecture Notes in Computer Science, Springer, pgs.728-735, herein incorporated by reference in its entirety. This method relies on a combination of temporal Fourier analysis of cine images with contour detection to achieve a fast localization of the heart.

Temporal Fourier analysis together with low level image processing techniques allow for the left ventricle blood pool localization in each axial slice. Therefore, the detection results in the different axial slices define the location and orientation of the left ventricle in the 3D space.

Such a method could be easily extended to detect also the right ventricle position, obtaining in this way also an approximation of the mitrel and pulmonary valve.

Another alternative method for determination of the heart valves is to the use of the velocity information in the 4D MR Flow data to localize rapid local velocity alterations. During specific periods in the cardiac cycle velocity alterations are expected for specific valves.

Just before the start of the systolic phase, the blood in the ventricle and the aortic artery and the pulmonary artery is almost stationary. At the start of the systolic phase, the blood is forced from the left and right ventricle in the aortic artery and the pulmonary artery respectively. This results in a major acceleration of the stationary blood from the ventricles into the artery and also the blood in the arteries is accelerated. The aortic artery and the pulmonary artery are large vessels and can be assumed as cylindrical shaped objects. The acceleration of the blood and the consequently increase in the blood velocity plus the presumed cylindrical shape can be detected in the 4D MR Flow data. After detecting both the aortic artery and pulmonary artery, the valve location is determined by tracking the blood flow upstream in both arteries. The aortic valve and the pulmonary valve location are determined at the transition of the ventricular volume and artery.

After the systolic phase the aortic valve and the pulmonary valve close and the mitrel valve and the tricuspid valve open. This results in rapid filling of the ventricles with blood from the atria. A major blood volume flows from the atrial volume to the ventricle volume through the valve opening. The valve opening is much smaller with respect to the atrial volume and the ventricular volume. The moment the mitrel valve or tricuspid valve opens the blood in the atria starts to accelerate and reaches a maximum velocity during the passage through the heart valves and the blood velocity will decelerate in the ventricles. The rapid ventricular filling results in a local concentrated high blood flow velocity in the valvular opening. The locations of the concentrated high velocities can be detected in the 4D MR Flow data. The mitrel valve and tricuspid valve location is determined at the center of the detected high velocity locations.

The determined valve locations in the 4D MR Flow data are transferred onto the axial cine MR image data to initialize the valve location based on the geometric information obtained from the DICOM (Digital Imaging and Communications in Medicine) header in which the MR image data is stored. Besides valve determination the combination of 4D MR Flow data and axial cine MR data enables the possibility for spatial registration of anatomical features to compensate for spatial offset induced by respiratory motion.

When the valve position has been determined in at least one axial cine MR image frame, the valve motion during the cardiac cycle is tracked (operation 104 of FIG. 1a).

A further improvement of the described approach consists in tracking the valve motion during the image post processing phase instead of during the scanning time. A failure of the tracking algorithm could namely become critical if the tracking takes place during scanning time, as described in Dewan et al, "*Deformable Motion Tracking of Cardiac Structures (DEMOTRACS) for Improved MR Imaging,*" IEEE Conference on Computer Vision and Pattern Recognition, 2007, herein incorporated by reference in its entirety. Such failure can lead to a misplaced acquisition plane and consequent irreparable inaccurate image data.

Instead, in our approach the valve tracking takes place during the post processing phase within the axial cine MR image data, where a possible failure could be easily identified and corrected.

The valve motion during the cardiac cycle can be followed in long axis images, using template matching approaches as described by Maffessanti et al. "*Three-dimensional dynamic assessment of tricuspid and mitral annuli using cardiovascular magnetic resonance,*" European Heart Journal—Cardiovascular Imaging (2013), Vol. 14, Issue 10, pp. 986-995, herein incorporated by reference in its entirety, and Dewan et al, "*Deformable motion tracking of cardiac structures (DEMOTRACS) for improved MR imaging,*" Computer Vision and Pattern Recognition, 2001, pgs. 1-8, herein incorporated by reference in its entirety.

In both methods the valve landmarks are manually appointed in a single image frame. At the marked locations, an image template is created with a fixed size. This image template is matched with a reference template. This reference template is obtained in two different manners as described by Maffessanti and Dewan.

The method of Dewan makes use of a multiple template matching approach where the reference templates are available in a template data base. Using multiple templates makes the method less sensitive for noise and acquisition artifacts. The valve tracking will take place by registration of the acquired long axis image templates per time frame with the multiple templates stored in the data base.

On the other hand, Maffessanti makes use of reference templates extracted from the acquired long axis image, with the assumption that the adjacent image has the most similarity with the previous image in time. This approach is sensitive for noise, artefacts and out of plane motion. The actual template matching is executed by using normal cross correlation.

In the valve tracking approach in accordance with embodiments herein, the idea of multiple template matching is adopted from Dewan and combined with the idea of using reference templates of the cine axial MR data set instead of reference templates in a data base from Maffessanti. The presented template matching methods of Dewan and Maffesanti are only applied to long axis images. These long axis images are restricted to two dimensions, for the axial cine image data however the approach needs to be extended to the third dimension.

This results in a template matching approach in which the templates are no longer two dimensional images but become three dimensional volumetric image features. The size of the templates is not fixed, but is adapted to the image acquisition resolution. Template matching can be performed, for instance, by use of normal cross correlation.

Once the at least one valve has been tracked in the anatomical data, for every time moment a spatial orientation of the valve plane is known. To be able to perform any blood flow analysis, the valve plane orientation of the anatomical data has to be defined in the 4D MR Flow data (step 105 of FIG. 1*b*).

The 4D MR flow data allows to retrospectively analyze the hemodynamic parameters at any location within the 3D data volume. For the quantification of valvular flow parameters, 2D analysis planes need to be positioned at the valve of interest.

Figure 4:
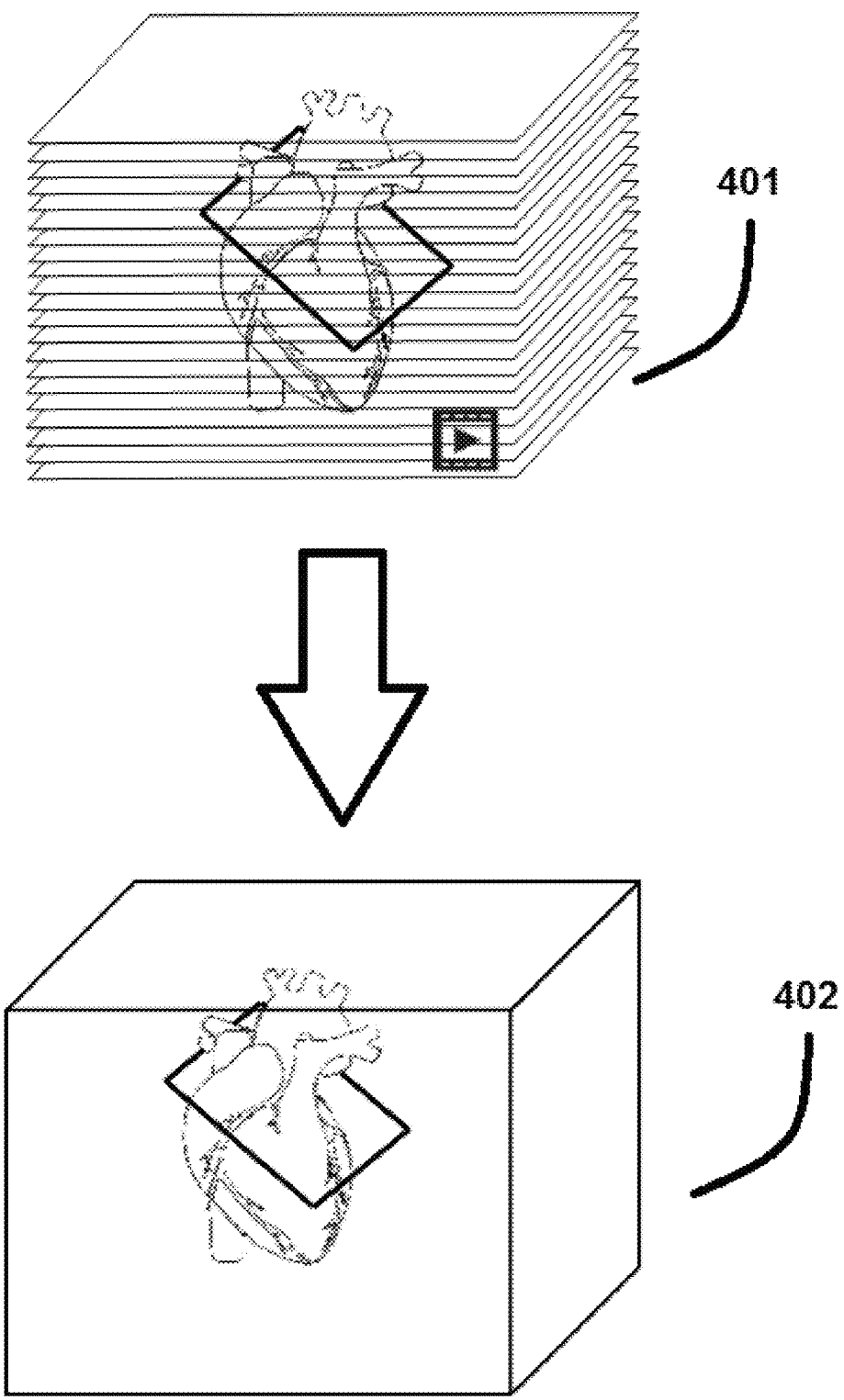
FIG. 4 shows the definition of the valve plane in the 4D MR Flow data using the axial cine MR image data.

In embodiments herein, the valve plane position and orientation is determined by the tracking algorithm, which yields a different plane definition for each cardiac phase. The defined analysis planes can, for instance, be transferred from the axial cine MR Image data (401) into the 4D MR flow data (402) as shown in FIG. 4. In an embodiment the plane is transferred from the axial cine MR to the 4D MR flow data based on the geometric information obtained from the DICOM header in which the MR image data is stored. Further optimization of the transferred plane, for instance to correct for patient movement which may occur between the acquisition of axial cine MR image data and the acquisition of the 4D MR flow image data, may involve image registration techniques such as described by Ding et al *"Volumetric image registration by template matching,"* Proc. SPIE 3979, Medical Imaging 2000: Image Processing, 1235 (Jun. 6, 2000), herein incorporated by reference in its entirety.

Once that the dynamic valve plane position and orientation has been defined in the 4D MR flow data, the plane orientation is optimized to preserve its perpendicularity to the blood flow (step 106 of FIG. 1*b*), following the method described in Calkoen et al.,*"Characterization and Improved Quantification of Left Ventricular Inflow Using Streamline Visualization With 4DFlow MRI in Healthy Controls and Patients After Atrioventricular Septal Defect Correction,"* J Magn Reson Imaging., June 2015, 41(6), pgs. 1512-20, herein incorporated by reference in its entirety.

This operation improves the accuracy of the blood flow estimation. A bias in the orientation of the analysis plane would lead to an underestimation of flow properties together with a misinterpretation of characteristic flow patterns. The anatomical dataset and the 4D MR Flow dataset could for instance consist of a non-rigid spatial offset or a different cardiac state because these datasets were acquired subsequently and not simultaneously. Optimizing the plane orientation, accounts for these artefacts.

Figure 5:
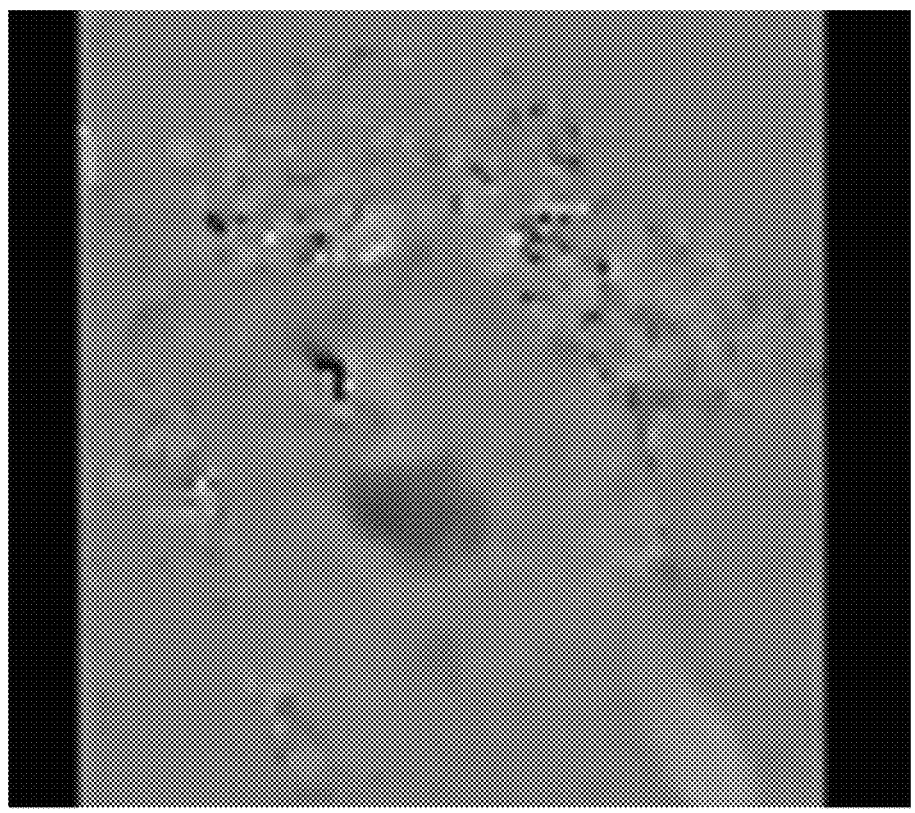
FIG. 5 shows a representation of the reformatted three-directional velocity information from 4D MR Flow data.

On such a plane the three-directional velocity information is reformatted into only one directional (through-plane) velocity data (step 107 of FIG. 1*b*), since for the quantification of flow the through plane is required. This can be done in the same manner as described in Westenberg et al., *"Mitral valve and tricuspid valve blood flow: accurate quantification with* 3*D velocity-encoded MR imaging with retrospective valve tracking,"* Radiology, December 2008, 249(3), pgs. 792-800, herein incorporated by reference in its entirety. An example of a representation of the reformatted three-directional velocity information from 4D MR Flow data is shown in FIG. 5. The reformatted one directional velocity data can represent both forward and backward flow.

Once the velocity information has been reformatted on a 2D dynamic analysis plane for every cardiac phase, quantitative flow analysis is performed (step 108 of FIG. 1*b*).

Before being able to perform quantitative flow analysis, the borders of the valve annulus have to be defined. This can be done manually or automatically by fitting a spline through the valve positions obtained earlier in the axial cine MR image data as described by Lee, *"A simplified B-spline computation routine,"* Computing 1982, Volume 29, Issue 4, pp 365-371, herein incorporated by reference in its entirety.

Subsequently, the velocity information obtained from the reformatted velocity data within the defined annulus area is used to quantify standard clinical parameters such as mean velocities, total flow, net flow or retrograde flow.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. Method for performing flow analysis in a target volume of a moving organ from sequences of a first and a second magnetic resonance volumetric image data sets of such organ, which data sets are timely separated by a certain time interval, wherein the first volumetric image data sets comprise structural information and three-directional velocity information of the target volume and the second volumetric image data sets comprises structural information of the target volume, the method comprising:
   a) determining at least one feature of interest in at least one volume data set of the sequence of second volumetric image data sets;
   b) tracking the feature of interest within one or more volume data sets of the sequence of the second volumetric image data sets;
   c) determining the spatial orientation over time of a plane containing the feature of interest in the sequence of the second volumetric image data sets;
   d) determining the spatial orientation over time of the plane containing the feature of interest in the sequence of the first volumetric image data sets by transferring the plane from the second volumetric image data sets to the first volumetric image data sets;
   e) reformatting the three-directional velocity information into one-directional velocity information on the plane as determined in step d); and
   f) performing bi-dimensional quantitative flow analysis using the one-directional velocity information.

2. Method according to claim 1, wherein:
the feature of interest is determined by receiving an input from a user or by performing automatic detection steps on at least one volume of the sequence of second volumetric image data sets.

3. Method according to claim 2, wherein:
the automatic detection steps comprise segmenting the moving organ or making a contour analysis of the same.

4. Method according to claim 1, wherein:
a location of the feature of interest in the first volumetric image data sets is determined from the three-directional velocity information and transposed to determine a location of the feature of interest in the second volumetric image data sets.

5. Method according to claim 1, wherein:
the operation b) of tracking the feature of interest involves matching multiple volumetric templates in the second volume image data sets.

6. Method according to claim 5, wherein:
the volumetric templates have a variable size depending on image acquisition resolution.

7. Method according to claim 1, wherein:
the orientation of the plane containing the feature of interest in the first volumetric image data sets is adjusted to render it perpendicular to a flow through the feature of interest.

8. Method according to claim 1, wherein:
the moving organ is the heart, the target volume is a region of the heart comprising a valve, and the feature of interest is the valve.

9. Method according to claim 8, wherein:
the first volumetric image data sets comprise anatomical information and three-directional blood velocity information of a heart volume, and the second volumetric image data sets comprises only anatomical information of the same or different heart volume.

10. Method according to claim 8, further comprising:
registering anatomical features in the first and second volumetric image data sets to compensate for spatial offset induced by motion.

11. Method according to claim 1, wherein:
the sequence of the first magnetic resonance volumetric image data sets is a 4D MR flow data set, and the sequence of the second magnetic resonance volumetric image data sets is an axial cine MR image dataset.

12. A non-transitory computer-readable storage medium loadable into memory of a digital computer and comprising software code portions for performing method steps when executed on the digital computer, wherein the method steps involve flow analysis in a target volume of a moving organ and comprise:
   a) obtaining sequences of first and second magnetic resonance volumetric image data sets of the moving organ, which data sets are timely separated by a certain time interval, wherein the first volumetric image data sets comprise structural information and three-directional velocity information of the target volume, and wherein the second volumetric image data sets comprises structural information of the target volume;
   b) determining at least one feature of interest in at least one volume data set of the sequence of second volumetric image data sets;
   c) tracking the feature of interest within one or more volume data sets of the sequence of the second volumetric image data sets;
   d) determining the spatial orientation over time of a plane containing the feature of interest in the sequence of the second volumetric image data sets;
   e) determining the spatial orientation over time of the plane containing the feature of interest in the sequence of the first volumetric image data sets by transferring the plane from the second volumetric image data sets to the first volumetric image data sets;
   f) reformatting the three-directional velocity information into one-directional velocity information on the plane as determined in step e); and
   g) performing bi-dimensional quantitative flow analysis using the one-directional velocity information.

13. MR apparatus comprising:
an acquisition system for obtaining sequences of first and second magnetic resonance volumetric image data sets of a patient's heart, which data sets are timely separated by a certain time interval, wherein the first volumetric image data sets comprise structural information and three-directional velocity information of a target volume of the patient's heart, and wherein the second volumetric image data sets comprises structural information of the target volume; and
a processing module programmed for
   a) determining at least one feature of interest in at least one volume data set of the sequence of second volumetric image data sets;
   b) tracking the feature of interest within one or more volume data sets of the sequence of the second volumetric data sets;
   c) determining the spatial orientation over time of a plane containing the feature of interest in the sequence of the second volumetric data sets;
   d) determining the spatial orientation over time of the plane containing the feature of interest in the sequence of the first volumetric data sets by transferring the plane from the second volumetric image data sets to the first volumetric image data sets;
   e) reformatting the three-directional velocity information into one-directional velocity information on the plane as determined in step d); and
   f) performing bi-dimensional quantitative flow analysis using the one-directional velocity information.

14. MR Apparatus according to claim 13, wherein:
the sequence of the first volumetric image data sets is a 4D MR flow data set, the sequence of the second volumetric image data sets is an axial cine MR image dataset, the target volume is a region of the heart comprising a valve, and the feature of interest is the valve; and
the processing module is programmed to determine the orientation of a valve plane in the axial cine MR image dataset, locate the valve plane in the 4D MR flow data set and make the bi-dimensional flow analysis based on the one-directional velocity information as projected on the valve plane.

15. MR Apparatus according to claim 14, wherein:
the orientation of the valve plane is determined by the processing module by performing valve tracking after the sequences of first and second volumetric image data sets have been acquired.

* * * * *